US009989482B2

(12) United States Patent
Abbott et al.

(10) Patent No.: US 9,989,482 B2
(45) Date of Patent: Jun. 5, 2018

(54) METHODS FOR RADIOGRAPHIC AND CT INSPECTION OF ADDITIVELY MANUFACTURED WORKPIECES

(71) Applicant: GENERAL ELECTRIC COMPANY, Schenectady, NY (US)

(72) Inventors: David Henry Abbott, Cincinnati, OH (US); Nicolas Kristopher Sabo, Cincinnati, OH (US)

(73) Assignee: General Electric Company, Schenectady, NY (US)

( * ) Notice: Subject to any disclaimer, the term of this patent is extended or adjusted under 35 U.S.C. 154(b) by 255 days.

(21) Appl. No.: 15/044,921

(22) Filed: Feb. 16, 2016

(65) Prior Publication Data

US 2017/0234812 A1    Aug. 17, 2017

(51) Int. Cl.
*G01N 23/04* (2018.01)
*G01N 23/083* (2018.01)

(52) U.S. Cl.
CPC ......... *G01N 23/083* (2013.01); *G01N 23/046* (2013.01); *G01N 2223/404* (2013.01); *G01N 2223/63* (2013.01); *G01N 2223/646* (2013.01)

(58) Field of Classification Search
CPC ......... G01N 2223/63; G01N 2223/404; G01N 2223/646; G01N 2223/41; G01N 2223/628; A61B 6/482
See application file for complete search history.

(56) References Cited

U.S. PATENT DOCUMENTS

| | | | |
|---|---|---|---|
| 3,197,638 A | 7/1965 | Sinclair | |
| 3,351,760 A | 11/1967 | Brown | |
| 3,704,370 A | 11/1972 | Shelton | |
| 4,079,124 A | 3/1978 | Winchell | |
| 4,582,993 A | 4/1986 | Bhattacharya et al. | |
| 4,810,447 A | 3/1989 | Csillag | |
| 4,819,256 A | 4/1989 | Annis et al. | |
| 4,832,708 A | 5/1989 | Csillag | |
| 6,619,368 B1 | 9/2003 | Springgate et al. | |
| 8,553,836 B2 | 10/2013 | Keller et al. | |
| 8,873,701 B2 * | 10/2014 | Mikhailov | G01N 33/24 378/4 |
| 2014/0005533 A1 | 1/2014 | Grasruck et al. | |
| 2014/0163717 A1 | 6/2014 | Das et al. | |

OTHER PUBLICATIONS

Paul J. Schilling et al., "X-ray computed microtomography of internal damage in fiber reinforced polymer matrix composites," Composites Science and Technology, 2005, vol. 65, pp. 2071-2078.
S. Van Bael et al., "Micro- CT-based improvement of geometrical and mechanical controllability of selective laser melted Ti6AI4V porous structures," Materials Science and Engineering A, 2011, vol. A 528, pp. 7423-7431.
Brenizer, J. S., et al., "The use of contrast agents to enhance crack detection via neutron radiography," NDT&E International, vol. 32, No. 1, pp. 37-42 (1999).
Sim, C.M., et al., "Detecting Internal Hot Corrosion of In-service Turbine Blades Using Neutron Tomography with Gd Tagging," Journal of nondestructive evaluation, vol. 33, No. 4, pp. 493-503 (2014).
Extended European Search Report and Opinion issued in connection with corresponding EP Application No. 17155845.5 dated Jun. 9, 2017.

* cited by examiner

*Primary Examiner* — Don Wong
(74) *Attorney, Agent, or Firm* — General Electric Company; Brian P. Overbeck

(57) ABSTRACT

The present disclosure generally relates to methods for radiographic and computed tomography (CT) inspection of workpieces having increasingly complicated internal geometry. The disclosed methods are capable of distributing a contrast agent within the detailed internal geometry of, for example, an AM workpiece or precision cast turbine blade, followed by complete removal of the contrast agent and all residues thereof after inspection.

15 Claims, No Drawings

METHODS FOR RADIOGRAPHIC AND CT INSPECTION OF ADDITIVELY MANUFACTURED WORKPIECES

INTRODUCTION

The present disclosure generally relates to methods for radiographic and computed tomography (CT) inspection of workpieces having internal geometry. The disclosed methods are capable of distributing a contrast agent within the internal geometry of, for example, an AM workpiece and/or precision cast turbine blade, followed by complete removal of the contrast agent and all residues thereof after inspection.

BACKGROUND

Many modern engines and next generation turbine engines require components and parts having intricate and complex geometries, which require new types of materials and manufacturing techniques to produce.

A turbine blade typically includes hollow airfoils that have radial channels extending along the span of a blade having at least one or more inlets for receiving pressurized cooling air during operation in the engine. Among the various cooling passages in the blades, including serpentine channels disposed in the middle of the airfoil between the leading and trailing edges, the airfoil typically includes inlets extending through the blade for receiving pressurized cooling air, which include local features such as short turbulator ribs or pins for increasing the heat transfer between the heated sidewalls of the airfoil and the internal cooling air.

The manufacture of these turbine blades, typically from high strength, superalloy metal materials, involves numerous steps. First, a precision ceramic core is manufactured to conform to the intricate cooling passages desired inside the turbine blade. A precision die or mold is also created which defines the precise 3-D external surface of the turbine blade including its airfoil, platform, and integral dovetail. The ceramic core is assembled inside two die halves which form a space or void therebetween that defines the resulting metal portions of the blade. Wax is injected into the assembled dies to fill the void and surround the ceramic core encapsulated therein. The two die halves are split apart and removed from the molded wax. The molded wax has the precise configuration of the desired blade and is then coated with a ceramic material to form a surrounding ceramic shell. Then, the wax is melted and removed from the shell leaving a corresponding void or space between the ceramic shell and the internal ceramic core. Molten superalloy metal is then poured into the shell to fill the void therein and again encapsulate the ceramic core contained in the shell. The molten metal is cooled and solidifies, and then the external shell and internal core are suitably removed leaving behind the desired metallic turbine blade in which the internal cooling passages are found.

Other jet aircraft engine parts, such as fuel nozzles, have recently been manufactured using AM techniques that involve the buildup of one or more materials to make a net or near net shape (NNS) object, in contrast to subtractive manufacturing methods. AM techniques are capable of fabricating complex components from a wide variety of materials. Generally, a freestanding object can be fabricated from a computer aided design (CAD) model. Applications include direct manufacturing of complex workpieces, patterns for investment casting, metal molds for injection molding and die casting, and molds and cores for sand casting. Fabrication of prototype objects to enhance communication and testing of concepts during the design cycle are other common usages of AM processes.

The increasingly complex internal geometry of aircraft engine parts has led to difficulties in the inspection of produced parts. Moreover, the migration of AM techniques from prototyping operations to full manufacturing production processes has created a need for more advanced techniques for non-destructive testing of the manufactured parts. As the workpieces have increased in size and the internal geometry of the produced workpieces has become more complex, a need has arisen for more powerful radiographic and CT inspection techniques.

The use of contrast agents for medical CT and radiographic inspection is known. CT imaging of manufactured parts relied on zinc iodide contrast agents. See Schilling et al., "X-ray computed microtomography of internal damage in fiber reinforced polymer matrix composites," Composites Science and Technology 65 (2005) 2071-2078. Zinc iodide is a commonly used contrast agent for CT scanning. CT inspection has been used on certain additively manufactured parts using conventional techniques. See Van Bael et al., "Micro-CT based improvement of geometrical and mechanical controllability of selective laser melted Ti5Al4V porous structures," Materials Science and Engineering (2011) 7423-7431.

The present inventors have found that traditional CT contrast agents lose their effectiveness in CT inspection as the complexity of the internal geometry and the overall size of the part increases. As advancements in additive manufacturing have led to larger workpieces having more complicated internal geometry, traditional methods of CT inspection lose their effectiveness. There is a need for industrial contrast agents and methods of inspection using these agents, particularly with respect to large-scale additively manufactured parts or precision cast workpiece, that are capable of depositing a contrast agent within the internal geometry of the workpiece, and removing the contrast agent through a process that is non-destructive to the workpiece after inspection.

SUMMARY

The present invention relates to an inspection method. The inspection method includes steps of applying a contrast slurry comprising a contrast agent to a workpiece having at least one internal passage; depositing the contrast agent or an oxide thereof within the internal passage; inspecting the workpiece using a radiographic inspection technique; and removing the contrast agent from the internal passage of the workpiece.

In one embodiment, the contrast agent is tungsten or a tungsten alloy. In another embodiment, the contrast agent is osmium or an osmium alloy. The contrast agent may oxidize, and the liquid portion may evaporate after heating. In one aspect of the invention, removing the contrast agent includes a leaching process, which may entail rinsing and/or submersing the workpiece in a bath with an agent such as hydrofluoric acid or acid or ammonia.

In one embodiment, the contrast agent comprises osmium, the heating forms osmium oxides, and the leaching is performed with an ammonium rinse. In one embodiment, the contrast agent comprises tungsten, the heating forms tungsten oxides, and the leaching is performed using hydrofluoric acid. The workpiece comprises iron, steel, cobalt chromium, Inconel, aluminum, and titanium.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

The present invention relates to a method of inspecting workpieces using CT or another radiographic method. The method uses a contrast agent for non-destructive inspection, the contrast agent includes one or more high-atomic numbered metals (e.g., tungsten or osmium) suspended or dissolved in a liquid carrier. The contrast agent must be non-reactive with the base metal of the workpiece to be inspected (e.g. aluminum, cobalt, nickel). The liquid carrier may be water or an organic solvent either alone or in combination with a suspending agent. The process of the present invention is capable of providing definitive evidence of an indication in a workpiece without the need to run subsequent testing to determine if an indication is a thru-crack or a thin-wall that was below the resolution of the radiographic method absent the contrast agent.

The contrast agent can be introduced to the workpiece using a pump or gravity feed via a fixture into the test article. The contrast agent is then deposited at least in part within one or more internal passages in the workpiece. The workpiece is then inspected using a radiographic method (e.g., CT scanning). After inspection, the contrast agent is removed from the part. The removal of the contrast agent may include flushing or using a pressurized cleaning or rinse solution.

In one embodiment, the process involves a curing (i.e., heating) step that allows the contrast agent to fill and adhere to surface indications. Because the contrast agents of the present invention allow for higher resolution inspection, defects that could not have been seen or fully characterized without the agent may be detected and characterized. This eliminates additional costly validation, testing, and/or inspection steps.

The workpiece according to the invention may be a part additively manufactured using direct laser melting or DMLM, such as an additively manufactured fuel nozzle. The workpiece may be a cast component such as a superalloy turbine blade. Any industrially manufactured structure having internal passages, particularly metallic structures, may benefit from the higher resolution inspection afforded by the present invention.

In the case of an AM workpiece, such as a part manufactured using a powder bed laser melting process (e.g., a fuel nozzle for a jet aircraft engine), the inspection method may follow making the part using a process involving forming the workpiece on a layer-by-layer basis using a process including steps of: (a) irradiating a layer of powder in a powder bed to form a fused region; (b) providing a subsequent layer of powder over the powder bed by passing a recoater arm over the powder bed from a first side of the powder bed; and (c) repeating steps (a) and (b) until the workpiece is formed in the powder bed, and (d) removing the workpiece from the powder bed. Additional steps such as heat treatment or cleaning may take place prior to inspection. Alternatively, these post-processing steps can take place after inspection in accordance with the present invention.

Where the workpiece is made in a precision casting process (e.g., turbine blade), the inspection method may follow making the part using a process involving steps of: (a) pouring a liquid metal (e.g., superalloy) into a casting mold and solidifying to form a cast component around the casting core and an outer shell mold, and (b) removing the outer shell mold and casting core. These removal steps may occur using mechanical (breaking) and/or chemical (leaching) processes. Additional steps such as heat treatment or cleaning may take place prior to inspection. Alternatively, these post-processing steps can take place after inspection in accordance with the present invention. The casting mold may be made using a lost-wax process involving surrounding at least a portion of the casting core with a disposable pattern material (e.g. wax or plastic) to form a core assembly, forming the outer shell mold around the core assembly, and removing the disposable pattern material from the outer shell mold.

The inspection method of the present invention allows for inspection of a variety of materials, mainly metals having internal cavities that make radiographic inspection difficult. For example, workpieces or parts may have internal cavities with thin walls. The present invention is useful for inspecting for potential indications such as cracks in those walls.

The application of contrast slurry may occur by way of a gravity feed to the part or by way of a pump. The slurry may be applied directly to an opening of the part exposing its internal cavities. Alternatively, the slurry may be added by way of a fixture attached to the part or workpiece. The slurry is designed to distribute the contrast agent throughout the internal cavities of the workpiece. In one embodiment, the contrast agent is tungsten or a tungsten alloy. In another embodiment, the contrast agent is osmium or an osmium alloy. The slurry may include other agents such as suspending agent or agents that aid in the ultimate removal of the slurry after inspection.

The contrast agent is deposited throughout the internal portions of the workpiece where inspection is desired. The deposition of contrast agent from the slurry may occur by flushing the part with slurry. Alternatively, the part may be heated after being filled or flushed with slurry. The heating step may be used to drive off the liquid portion of the slurry or some of the liquid portion. The heating may also react the contrast agent as applied to form another contrast agent. For example, if the contrast agent is tungsten, the heating may result in some or all of the tungsten to be converted to tungsten oxide ($WO_2$—$WO_4$). If the contrast agent is osmium, heating may cause the osmium to react to osmium oxide(s) ($OsO_2$—$OsO_4$). Alternatively, the contrast agent may be applied as a slurry of the metal oxide. In that case, the heating step may be unnecessary or used simply to evaporate some or all of the liquid in the slurry prior to inspection.

Once the contrast agent is added to the part or workpiece, and any heating or curing step performed, the part may be inspected using a radiographic method such as CT scanning. The inspection step is similar to those known in the art, except that a contrast agent allows for higher power scanning and increased resolution. The higher power allows for more powerful detection of flaws and can eliminate some of the testing required for industrial processes, particularly for parts being manufactured with AM techniques or precision casting technology.

After inspection, the contrast agent is removed. This can be done by flushing or rinsing the part with water. In the case where slurry is added via a fixture, the rinsing agent may be applied through the same fixture. The contrast agent in its cured form may be particularly susceptible to removal via a chemical leaching process. For example, where the contrast agent is tungsten oxide, it may be chemically removed using a rinse solution comprising an acid such as hydrofluoric acid. Where the contrast agent is an osmium oxide, the leaching agent may be an aqueous ammonia rinse. The rinse solution may be a combination of rinsing agents and may be used with other rinsing agents such as an organic solvent. For example, if the leaching is done using an aqueous solution of ammonia or hydrofluoric acid, there may be a subsequent rinse in an organic solvent to aid in the removal of water within the part.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Aspects from the various embodiments described, as well as other known equivalents for each such aspect, can be mixed and matched by one of ordinary skill in the art to construct additional embodiments and techniques in accordance with principles of this application.

The invention claimed is:

1. An inspection method comprising:
   applying a contrast slurry comprising a contrast agent to a workpiece having at least one internal passage;
   depositing the contrast agent or an oxide thereof within the internal passage of the workpiece;
   inspecting the workpiece using a radiographic inspection technique; and
   removing the contrast agent from the internal passage of the workpiece.

2. The method of claim 1, wherein contrast agent is tungsten or a salt or alloy thereof.

3. The method of claim 1, wherein contrast agent is osmium or a salt or alloy thereof.

4. The method of claim 1, wherein heating the workpiece oxidizes at least a portion of the contrast agent.

5. The method of claim 1, wherein depositing comprises heating the workpiece to vaporize at least a portion of the liquid of the slurry.

6. The method of claim 1, wherein removing comprises leaching.

7. The method of claim 2, wherein the leaching is performed with hydrofluoric acid or ammonia.

8. The method of claim 1, wherein the contrast agent comprises tungsten, the heating forms tungsten oxides, and the leaching is performed with a hydrofluoric acid rinse.

9. The method of claim 1, wherein the contrast agent comprises osmium, the heating forms osmium oxides, and the leaching is performed with an ammonium rinse.

10. The method of claim 1, wherein the workpiece comprises iron, steel, cobalt chromium, Inconel, aluminum, and titanium.

11. The method of claim 1, wherein prior to applying the contrast agent, the workpiece is formed on a layer-by-layer basis comprising steps of:
    (a) irradiating a layer of powder in a powder bed to form a fused region;
    (b) providing a subsequent layer of powder over the powder bed by passing a recoater arm over the powder bed from a first side of the powder bed; and
    (c) repeating steps (a) and (b) until the workpiece is formed in the powder bed, and
    (d) removing the workpiece from the powder bed.

12. The method of claim 1, wherein prior to applying the contrast agent, the workpiece produced using a precision casting process comprising the following steps:
    pouring a liquid metal into a casting mold and solidifying to form a cast component, the casting mold comprising a casting core and an outer shell mold; and
    removing the outer shell mold and casting core.

13. The method of claim 12, wherein removing the casting core comprises a step of leaching.

14. The method of claim 12, further comprising before pouring the liquid metal, preparing the casting mold using a process comprising the steps of:
    surrounding at least a portion of the casting core with a disposable pattern material to form a core assembly;
    forming the outer shell mold around the core assembly; and
    removing the disposable pattern material from the outer shell mold.

15. The method of claim 14, wherein the disposable pattern material is wax or plastic.

* * * * *